United States Patent [19]

Shoesmith

[11] Plant 5,076

[45] Jul. 26, 1983

[54] CHRYSANTHEMUM NAMED FIREBRAND (FP6-143-BS)

[75] Inventor: Leonard H. Shoesmith, Westfield-Woking, England

[73] Assignee: Pan American Plant Company, Parrish, Fla.

[21] Appl. No.: 312,887

[22] Filed: Oct. 19, 1981

[51] Int. Cl.[3] ..... A01H 5/00

[52] U.S. Cl. ..... Plt./74

[58] Field of Search ..... Plt./74

*Primary Examiner*—Robert E. Bagwill

*Attorney, Agent, or Firm*—Chas. W. Rummler

[57] ABSTRACT

A new and distinct bronze spoon-tipped chrysanthemum cultivar particularly adaptable for production as a six-inch pot plant. This plant has an exceptional growth habit and is very free breaking. It blooms profusely with a nine-week response and has flowers of a medium size.

4 Drawing Figures

BACKGROUND OF THE NEW PLANT

My new chrysanthemum cultivar originated as a seedling of unknown parentage and was discovered by me in 1976 at West Chicago, Ill., growing in a field of miscellaneous seedlings grown in greenhouse with the hope of finding new and interesting varieties that might have commercial merit. This plant was selected by me for propagation and test because of its very unusual spoon-tipped florets of a distinct bronze coloration carried at the end of a tube of contrasting color. Propagation of the discovery plant was done under my direction, by means of cuttings, at West Chicago, Ill., and continued propagation of this plant through successive generations, also by cuttings, has demonstrated that the novel characteristics of this plant hold true from generation to generation and appear to be firmly fixed. This plant is now being propagated on a commercial scale, by means of cuttings, at Cortez and Parrish, Fla.

DESCRIPTION OF THE DRAWINGS

My new chrysanthemum cultivar is illustrated by the accompanying drawings, of which sheet one is a photographic rendition of a potted plant in full bloom showing its general form at maturity and the nature of its blossoms; sheet two is a photographic print of a close-up view of one of the flowers of this plant which has been hand painted to show the true coloration of the blooms; sheet three is a print of a mechanical reproduction of the front side of typical leaves of this new plant; and sheet four is a similar print showing the back or under side of the leaves pictured on sheet three.

DESCRIPTION OF THE NEW PLANT

The following is a detailed description of my new chrysanthemum cultivar based upon observations of greenhouse grown plants at West Chicago, Ill., in the early Spring of 1981, the color designations being according to The R.H.S. Colour Chart published by The Royal Horticultural Society of London, England.

THE PLANT

Origin: Seedling.
Parentage: Unknown.
Classification:
- *Botanic.*—Chrysanthemum Morifolium.
- *Commercial.*—Pot Chrysanthemum.

Form: Perennial herbaceous bush of upright shape.
Height: Varies according to cultural treatment.
Growth: Vigorous and strong.
Growth rate: Typical chrysanthemum.
Branching character: Caespitose under normal conditions.
Foliage:
- *Quantity.*—Abundant.
- *Size of leaf.*—Up to about 95 mm. long and about 70 mm. wide.
- *Leaf shape.*—Ovate with cleft margins.
- *Texture.*—Leathery.
- *Ribs and veins.*—Pinnate.
- *Color.*—Upper side — 147A. Under side — 147B.
- *Petioles.*—Length — From insignificant to about 30 mm.

THE BUD

Form: Globular.
Size: Variable in both diameter and length.
Rate of opening: Typical chrysanthemum.
Color:
- *When phyllaries first divide.*—46A.
- *When florets begin to unfurl.*—46A.

Phyllaries:
- *Number.*—Approximately 23.
- *Shape.*—Lanceolate.
- *Color.*—138A.

Peduncle or flower stem:
- *Length.*—Variable.
- *Character.*—Rigid and erect.
- *Surface aspect.*—Pubescent.
- *Color.*—138A.

THE FLOWER

Blooming habit: Intermittent and blooms profusely.
Response: Nine weeks.
Blooms:
- *Size.*—Medium. Diameter — About 60 to 80 mm. Depth — Flat.
- *Borne.*—Cyme.
- *Shape or form.*—A bronze, spoon-tipped, single inflorescence borne on a receptacle surrounded by an involucre of bracts. When bloom first opens — Cup-shaped. When bloom matures — Flat.

Petalage:
- *Phyllaries.*—About 23 in number.

*Florets.*—About 25 ray florets and numerous disc florets.

*Arrangement.*—Imbricated.

*Form of floret.*—Spoon-tipped with rounded and ragged apex and smooth margin.

Texture: Soft.

Appearance: Satiny.

Color:

*Ray florets.*—Spoon: 46A (R.H.S.). Top side of tube: 160B (R.H.S.). Under side of tube: 161B (R.H.S.).

*Disc florets.*—Yellow.

Effect of wet or hot weather: This plant is temperature sensitive and will perform best under conditions where the temperature is easily controlled.

Discoloration after full bloom: The flower fades after reaching maturity.

Persistence: The florets hang on and dry.

Fragrance: Typical chrysanthemum.

REPRODUCTIVE ORGANS

Stamens:

*Number.*—Five.

*Arrangement.*—Syngenesious.

*Anthers.*—Size: Insignificant. Color: Yellow.

*Filaments.*—Of insignificant length and yellow color.

*Pollen.*—Yellow.

Pistils:

*Number.*—One for each floret.

*Styles.*—Of insignificant length and yellow color.

Stigmas:

*Color.*—Yellow.

Ovaries: Inferior and bicarpellate.

This plant is a new and distinctive chrysanthemum variety with bronze colored, spoon-tipped ray florets carried on long tubes of a contrasting yellow color. This plant has a nine-week response and is particularly suitable for production as a six-inch pot plant. Since this plant is temperature responsive, it will perform best under those conditions where the temperature is easily controlled, that is, generally in the Spring or Fall and in certain areas the year around.

I claim:

1. A new and distinct spoon-tipped chrysanthemum, substantially as herein shown and described, particularly characterized by the bronze coloration of its ray florets and its floriferous and vigorous growth habit.

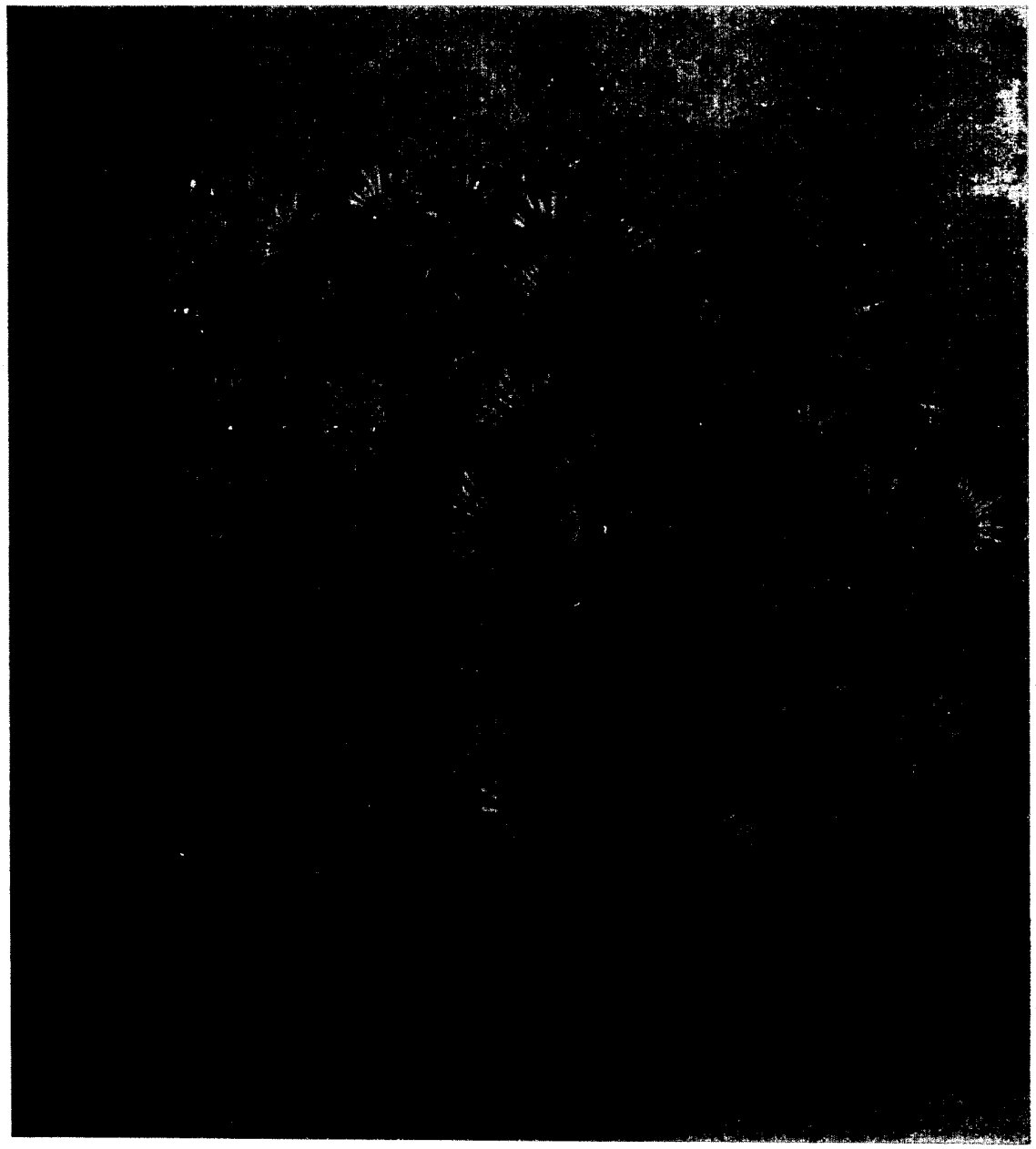

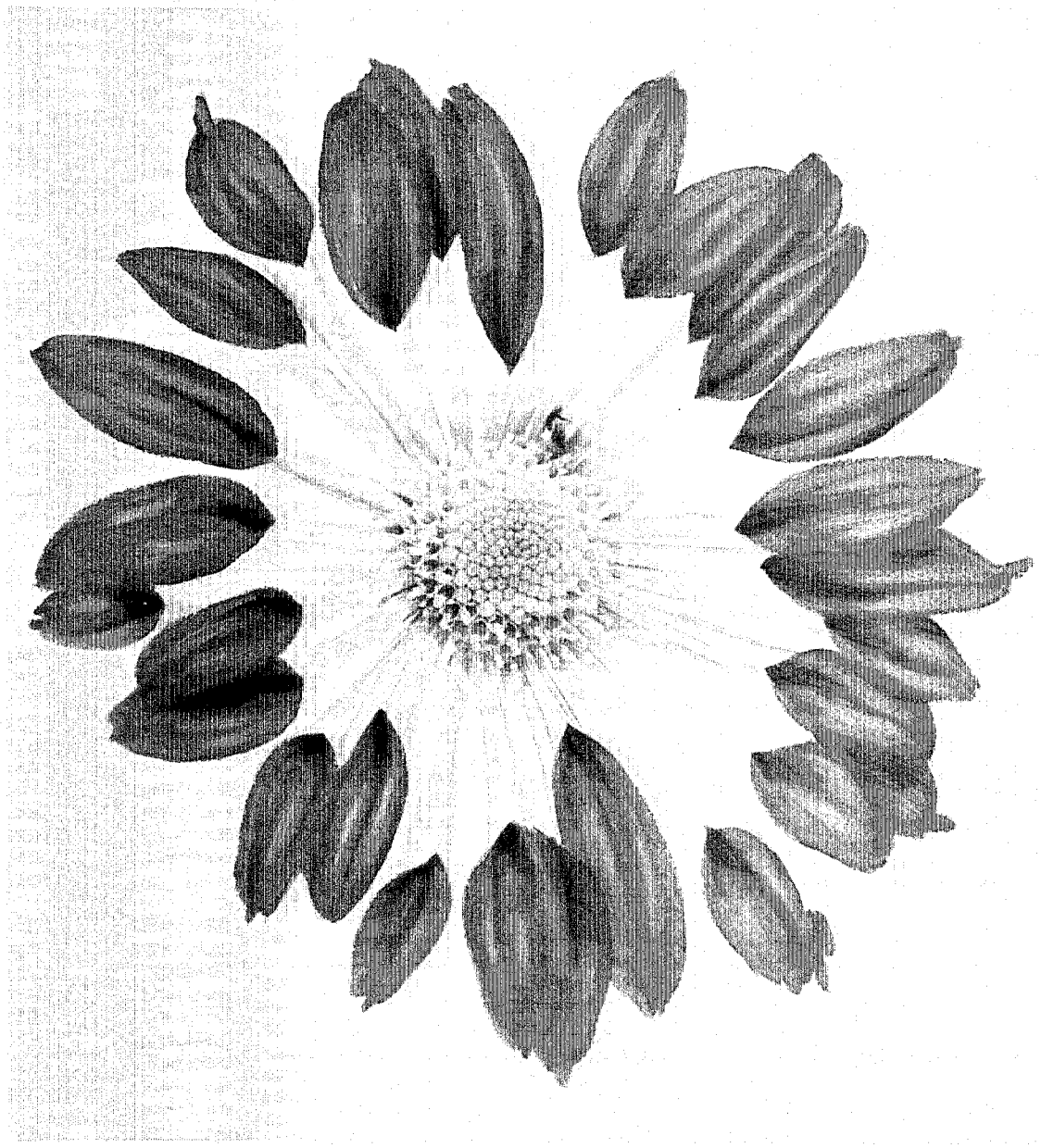

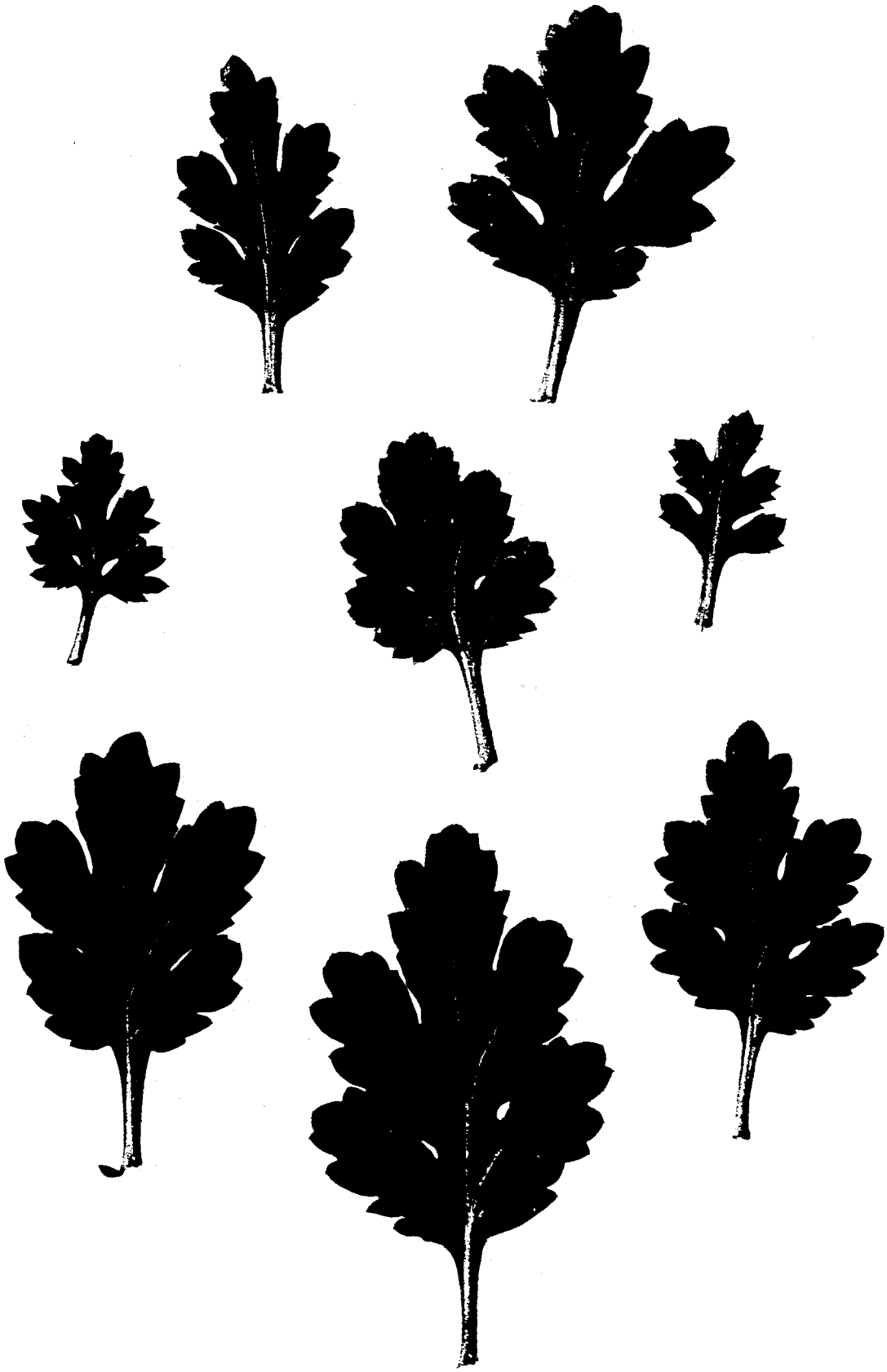

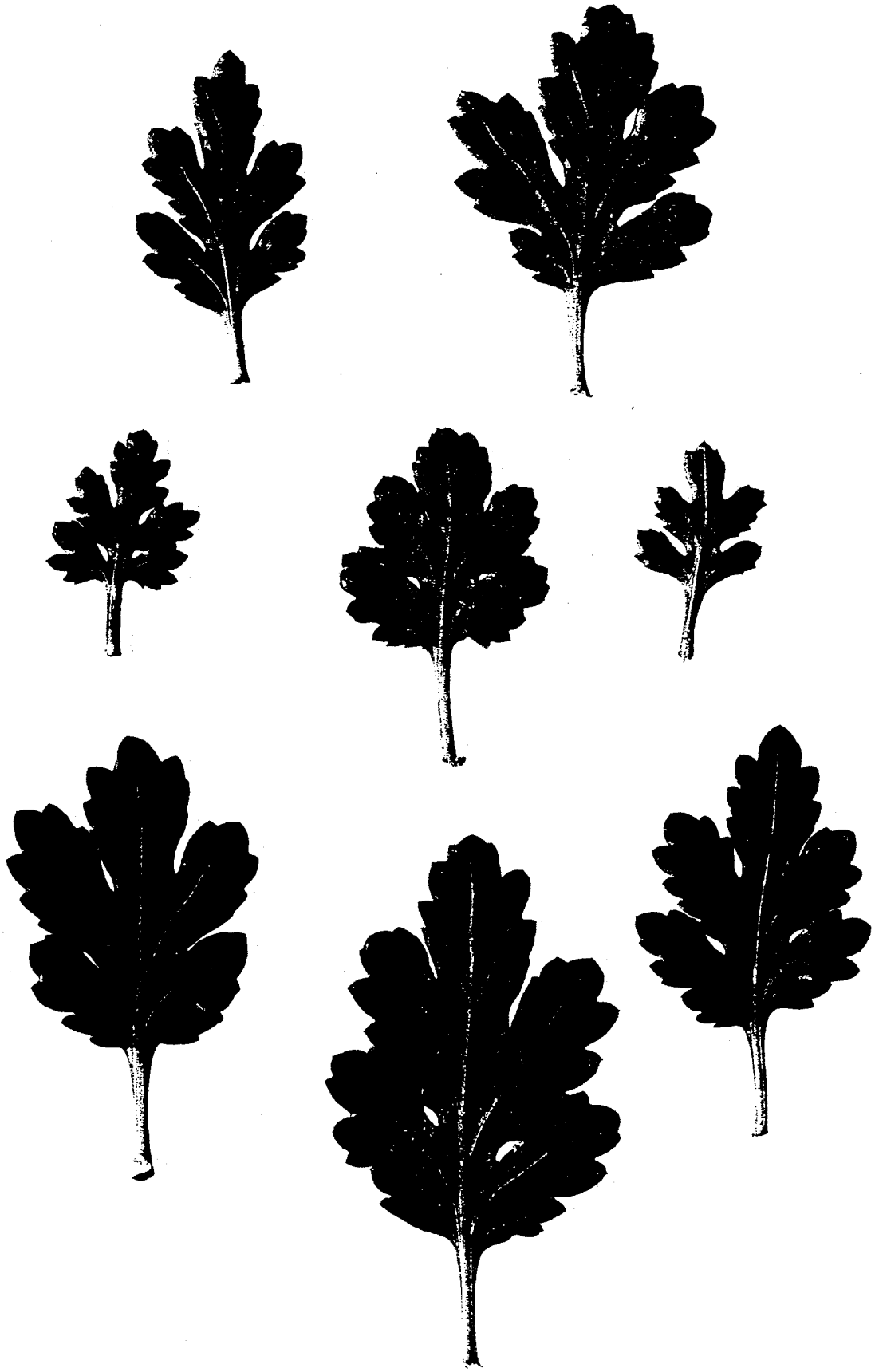

* * * * *